(12) United States Patent
Morgan et al.

(10) Patent No.: US 9,468,680 B2
(45) Date of Patent: Oct. 18, 2016

(54) DIFFERENTIAL EFFECTS OF DRUGS ON TRANSPORT IN A MULTI-LAYER 3D SPHEROID MODEL

(71) Applicant: Brown University, Providence, RI (US)

(72) Inventors: Jeffrey R. Morgan, Sharon, MA (US); Toni-Marie Achilli, Providence, RI (US); Anubhav Tripathi, Northborough, MA (US); Stephanie McCalla, Providence, RI (US)

(73) Assignee: Brown University, Providence, RI (US)

( * ) Notice: Subject to any disclaimer, the term of this patent is extended or adjusted under 35 U.S.C. 154(b) by 340 days.

(21) Appl. No.: 13/623,599

(22) Filed: Sep. 20, 2012

(65) Prior Publication Data

US 2013/0079288 A1    Mar. 28, 2013

Related U.S. Application Data

(60) Provisional application No. 61/538,069, filed on Sep. 22, 2011.

(51) Int. Cl.
*A61K 45/06* (2006.01)
*G01N 33/50* (2006.01)

(52) U.S. Cl.
CPC ........... *A61K 45/06* (2013.01); *G01N 33/5011* (2013.01)

(58) Field of Classification Search
CPC  C12N 5/0062; C12N 5/0671; C12N 5/0677; C12N 5/0602
See application file for complete search history.

(56) References Cited

U.S. PATENT DOCUMENTS

| | | | |
|---|---|---|---|
| 5,650,164 A | 7/1997 | Della Valle et al. | |
| 5,792,653 A | 8/1998 | Weibezahn et al. | |
| 7,887,843 B2 | 2/2011 | Libera et al. | |
| 8,361,781 B2 | 1/2013 | Morgan et al. | |
| 8,501,476 B2 | 8/2013 | Morgan et al. | |
| 2003/0049597 A1* | 3/2003 | Simon et al. | 435/4 |
| 2003/0153078 A1 | 8/2003 | Libera et al. | |
| 2004/0009537 A1 | 1/2004 | Roos | |
| 2005/0169962 A1 | 8/2005 | Bhatia et al. | |
| 2013/0109625 A1 | 5/2013 | Morgan et al. | |
| 2013/0137155 A1 | 5/2013 | Morgan et al. | |

FOREIGN PATENT DOCUMENTS

| | | |
|---|---|---|
| DE | 4132379 A1 | 4/1993 |
| EP | 1 367 119 B1 | 9/2008 |
| JP | 08-140673 A | 6/1996 |
| JP | 2000-069957 A | 3/2000 |
| JP | 2003-052361 A | 2/2003 |
| JP | 2004-089136 A | 3/2004 |
| JP | 2004-097047 A | 4/2004 |
| JP | 2004-121168 A | 4/2004 |
| JP | 2005-160596 A | 6/2005 |
| JP | 2006-055069 A | 3/2006 |
| WO | WO 95/31184 A1 | 11/1995 |
| WO | WO 99/52356 A1 | 10/1999 |
| WO | WO 03/059072 A1 | 7/2003 |
| WO | WO 2005/077013 A2 | 8/2005 |
| WO | WO 2007/087402 A2 | 8/2007 |

OTHER PUBLICATIONS

Martin et al. (British J. Cancer 2003 89:1581-1589).*
Oshikata et al. (J. Biosci. Bioengineering May 2011 111(5): 590-593).*
Gura (Science, 1997, 278:1041-1042).*
Kaiser (Science, 2006, 313: 1370).*
Dean, D. M., et al., "Rods, tori, and honeycombs: the directed self-assembly of microtissues with prescribed microscale geometries," *FASEB J.*, 21(14): 4005-4012 (2007).
English Translation of JP 2006-055069, downloaded from http://www4.ipdl.inpit.go.jp on Nov. 2, 2011.
Extended European Search Report from European Application No. 07762405.4, "Cell Aggregation and Encapsulation Device and Method." Date of Mailing: Sep. 22, 2009; 7 pages.
Folch, A., and Toner, M., "Microengineering of Cellular Interactions," *Annu. Rev. Biomed. Eng.*, 2(1): 227-256 (2000).
Fukuda, J., and Nakazawa, K., "Orderly Arrangement of Hepatocyte Spheroids on a Microfabricated Chip," *Tissue Engineering*, 11(7/8): 1254-1262 (2005).
International Search Report and Written Opinion of the International Searching Authority from International Application No. PCT/US2007/002050, "Cell Aggregation and Encapsulation Device and Method" . Date of Mailing: Jul. 9, 2008; 5 pages.
Jakab, K., et al., "Engineering biological structures of prescribed shape using self-assembling multicellular systems," *Proc. Natl. Acad. Sci. USA*, 101(9): 2864-2869 (2004).
Kelm, J. M., et al., "Tissue-Transplant Fusion and Vascularization of Myocardial Microtissues and Macrotissues Implanted into Chicken Embryos and Rats," *Tissue Engineering*, 12(9): 2541-2553 (2006).
Kelm, J. M., and Fussenegger, M., "Microscale tissue engineering using gravity-enforced cell assembly," *TRENDS in Biotechnology*, 22(4): 197-202 (2004).
Livoti, C. M. and Morgan, J. R., "Self-Assembly and Tissue Fusion of Toroid-Shaped Minimal Building Units," *Tissue Engineering: Part A*, 16(6): 2051-2061 (2010).
Mironov, V., et al., "Organ printing: computer-aided jet-based 3D tissue engineering," *TRENDS in Biotechnology*, 21(4): 157-161 (2003).
Napolitano, A. P., et al., "Dynamics of the Self-Assembly of Complex Cellular Aggregates on Micromolded Nonadhesive Hydrogels," *Tissue Engineering*, 13(8): 2087-2094 (2007).
Napolitano, A. P., et al., "Scaffold-free three-dimensional cell culture utilizing micromolded nonadhesive hydrogels," *BioTechniques*, 43(4): 494-500 (2007).

(Continued)

*Primary Examiner* — Peter J Reddig
(74) *Attorney, Agent, or Firm* — Hamilton, Brook, Smith & Reynolds, P.C.

(57) ABSTRACT

Drugs are screened for affects on inhibiting efflux pumps and blocking gap junction communication in tumors by culturing cells to thereby form self-assembled spheroids and incubating the spheroids. Uptake of a substrate of the efflux pump and distribution of a substrate for the efflux pump within the spheroids is imaged to thereby select drugs that inhibit the efflux pump or do not block gap junction communication. Selected drugs can then be employed to treat a tumor.

15 Claims, 9 Drawing Sheets
(4 of 9 Drawing Sheet(s) Filed in Color)

(56) References Cited

OTHER PUBLICATIONS

Rago, A. P., et al., "Miniaturization of an Anoikis assay using non-adhesive micromolded hydrogels," *Cytotechnology*, 56(2): 81-90 (2008).

Rago, A. P., et al., "Controlling Cell Position in Complex Heterotypic 3D Microtissues by Tissue Fusion," *Biotechnology and Bioengineering*, 102(4): 1231-1241 (2009).

Yeh, J., et al., "Micromolding of shape-controlled, harvestable cell-laden hydrogels," *Biomaterials*, 27(31): 5391-5398 (2006).

Abbaci, M., et al., "Advantages and limitations of commonly used methods to assay the molecular permeability of gap junctional intercellular communication," *BioTechniques*, 45(1):33-62, (Jul. 2008).

Notice of Allowance mailed on Oct. 15, 2015 for U.S. Appl. No. 13/623,668 entitled "Mechanotransduction By The Synergistic Action Of Heterotypic Cell Interactions".

Office Action from U.S. Appl. No. 12/896,173, mailing date Jun. 14, 2012.

Final Office Action from U.S. Appl. No. 13/623,668, mailing date Apr. 30, 2015.

Office Action for Canada Appl. No. 2,637,663 dated Jun. 28, 2013.

\* cited by examiner

DIFFERENTIAL EFFECTS OF DRUGS ON TRANSPORT IN A MULTI-LAYER 3D SPHEROID MODEL

RELATED APPLICATION

This application claims the benefit of U.S. Provisional Application No. 61/538,069, filed on Sep. 22, 2011. The entire teachings of the above application are incorporated herein by reference.

GOVERNMENT SUPPORT

This invention was made with government support under R01EB008664-01A1 awarded by National Institutes of Health. The government has certain rights in the invention.

BACKGROUND OF THE INVENTION

A quantitative understanding of mass transport is an important aspect of successful drug development and drug efficacy. At the cellular and multi-cellular level, diffusion is the primary mechanism for the transport of drugs to cells, avascular tissues, and tumors[1]. However, transport is tightly controlled by numerous biological barriers including the plasma membrane, receptors, transport proteins, channels, vesicular systems, cell adhesion molecules, gap junctions, and cellular efflux pumps[2,3]. A drug's ability to cross cell and tissue barriers in vivo is a key determinant of the absorption, distribution, metabolism, excretion, and toxicity (ADME-Tox), and, ultimately, the success of the drug[4-6]. From the route of administration to the site of action, a drug encounters numerous biological barriers and drug transporters before reaching its intended target. The largest class of transporters is the family of ATP binding cassette (ABC) transporters. Much is known about one of these members, namely, p-glycoprotein (Pgp or ABCB1).

P-glycoprotein is a transporter that is localized to the plasma membrane of cells and is present in both normal and diseased tissues[7,8]. In normal tissues, Pgp helps to protect sensitive tissues from toxicity by facilitating efflux and preventing the intracellular accumulation of Pgp substrates[8,9]. For example, Pgp is constitutively expressed in the blood-brain barrier (BBB), the blood-testis barrier (BTB), and the placental barrier[10-13]. While the normal function of Pgp is protection from toxicity, it is also a significant barrier to drug transport and delivery. Pgp is constitutively expressed in the intestine, liver, and kidney, which decreases the bioavailability and distribution of drugs by hindering absorption through the intestine and increasing clearance into bile and urine[5,8,14]. Additionally, Pgp is up-regulated in diseased tissues and the cells of solid tumors. There, Pgp increases resistance to anti-cancer chemotherapeutics[2,15]. Unfortunately, many drugs of various pharmacological classes are substrates of this pump[16].

Numerous inhibitors of Pgp have been identified, characterized extensively in vitro, tested in pre-clinical models, and evaluated in the clinic Although effective in vitro, Pgp inhibitors have been ineffective in the clinic, or have unexpected drug-drug interactions leading to increased toxicity[7,18]. There are three principal in vitro methods used to characterize inhibitors of Pgp: measurement of the efflux of radio-labeled compounds by a mono-layer of cells on a transwell dish, measurement of drug-stimulated ATPase activity of Pgp protein, and measurement of calcein-AM uptake by a mono-layer of cells[19-22]. Mono-layers of cells can measure inhibition of Pgp, but drug transport in these two-dimensional (2D) systems does not accurately replicate the complexity of the barriers found in a three-dimensional (3D) multi-cell layer environment. For example, the diffusion distance for a drug into a mono-layer of cells is relatively short compared to in vivo tissues and biological barriers are not adequately replicated in a 2D mono-layer. Moreover, there may be differential expression of Pgp in 2D culture versus 3D culture. Current methods to quantify 3D transport are cumbersome and include the use of microelectrode sensors to measure the concentration gradient of ions or monitoring the transport of radio-labeled molecules[23,24]. While these methods provide concentration profiles of a single plane through a tissue, they are time consuming and not amenable to higher throughput analyses because they rely on histological processing and contact autoradiography[25,26].

Current in vitro models used to test the effects of inhibitors of Pgp often use single cells or mono-layers of cells such as MDR1-MDCK cells, a polarized kidney epithelial cell transfected to overexpress Pgp[22]. Using single cells and mono-layers, studies have quantified transport and reaction parameters such as diffusivity[32], enzyme kinetics[33], and drug inhibition[34]. Transport properties, molecular gradients, and cellular gradients have also been obtained from 3D models, but these require more complex experimental and analytical procedures such as two-photon microscopy[35], incorporated probes[36], tissue sectioning[26], or mathematical models[37,38]. The 2D studies have also shown that verapamil ($IC_{50}$=60.9±8.91), loperamide, cyclosporin A ($IC_{50}$=2.2±0.02), and others are all effective inhibitors of Pgp at concentrations ranging from 1-100 μM using a calcein-AM assay, with percent maximum inhibition of 56.4%, 76.3%, and 98.7% respectively$_{b\ 19,20}$.

Since drug efflux transporters are expressed at numerous locations within various organs and can transport a wide range of structurally diverse drugs, unwanted and unexpected side effects may occur when two or more therapeutic drugs are administered[18]. For example, despite being a potent opiate, loperamide administered alone does not cause opiate-like effects. However, co-administration of loperamide and quinidine (another Pgp inhibitor) increases the transport of loperamide across the blood brain barrier and leads to respiratory depression[30]. Conversely, drug efflux transporters are often up-regulated by solid tumors and contribute to resistance to chemotherapeutic agents[2,15]. In this case, more effective inhibitors of efflux transporters are needed to increase the concentration of the chemotherapeutic drug in the tumor. For example, Pgp drug resistance to several chemotherapeutic classes[9,16], including vinca alkaloids, anthracyclines, and taxanes, has been observed in lymphoma, breast cancer, ovarian cancer, and small-cell lung cancer, as well as in tumors derived from tissues that constitutively express Pgp, such as colorectal cancer and renal cell carcinoma[17,31]. However, despite an important medical need, none of the well-known inhibitors of drug efflux transporters are currently used as an adjunct in the treatment of solid tumors either because they are clinically ineffective or they caused side effects, including increased toxicity, unwanted drug-drug interactions, or negative effects on the pharmacokinetics of the therapeutic[15]. Thus, there is a need for new in vitro models that can be used to predict potential toxicities and unwanted drug-drug interactions or to discover new and more effective inhibitors of drug efflux transporters.

Therefore, a need exists for a method and system to overcome or minimize the above-mentioned problems with the effect of candidate anticancer drugs on efflux pumps and gap channel communication.

SUMMARY OF THE INVENTION

The invention is generally directed to a method for screening for drugs that inhibit efflux pumps and do not block gap junctions in tumors, and to methods of treating tumors by use of drugs identified by the screening method.

In one embodiment, the invention is a method for treating a tumor that includes screening for a selected drug that has an effect of at least one of inhibiting an efflux pump and not blocking gap junctions in tumors. The screening method includes the steps of seeding a cell culture medium that includes a drug to be screened with cells in a non-adherent well to form a cell suspension. The cells are cultured to form self-assembled spheroids that have a core and an outer shell. The spheroids are incubated in the presence of a substrate for the efflux pump to thereby cause at least a portion of the substrate to penetrate the cell. Uptake of the substrate and the distribution of the substrate within the spheroids is imaged, whereby an increased concentration of the substrate in the outer shells of the spheroids relative to that of the total spheroids that self-assembled in the absence of the drug indicates that the drug inhibits the efflux pump, and an increase in substrate at the cores of the spheroids relative to that of spheroids that self-assembled in the absence of the drug indicates that gap junction communication has not been blocked by the drug. A drug that is identified as either inhibiting the efflux pump or not blocking gap junction communication is designated a selected drug. Optionally, administration of the selected drug to a tumor is enabled, thereby treating the tumor.

P-glycoprotein (Pgp) is an example of a regulator of the absorption, distribution, and excretion of clinically important drugs. Other suitable efflux pumps include any of the other 48-ATP-binding cassettes (ABC) in the human genome [49, 50, 51]. In diseased tissues, such as the cells of a solid tumor, Pgp is often up-regulated and increases the resistance to anti-cancer chemotherapeutics. Numerous inhibitors of Pgp have been identified using 2D mono-layers of cells, but there has been poor clinical translation due to a lack of efficacy or unwanted side effects in vivo. As described herein, three-dimensional (3D) multi-layer tumor spheroids that mimic physiological barriers of drug transport to study the effect of Pgp efflux inhibitors (verapamil, loperamide, and cyclosporin A). All three inhibitors increased the total uptake by spheroids.

The quantitative positional analysis described herein revealed that increased calcein was confined to the outermost layer of cells for spheroids treated with verapamil and loperamide. Only cyclosporin A treatment caused an increase in calcein concentration in the spheroid core Inhibiting gap junctions using carbenoxolone inhibited the transport of calcein into the spheroid core, and calcein transport was also blocked in cells that lack functional gap junctions (OVCAR-3 and SK-OV-3). These data suggest that in addition to blocking Pgp, verapamil and loperamide also block gap junctions, an activity not yet reported for these drugs. Quantitative 3D models that more accurately replicate in vivo barriers to drug transport may be useful for discovering new, more effective inhibitors of drug efflux transporters and may also be helpful in the early identification of possible side effects and drug-drug interactions of new drug candidates.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
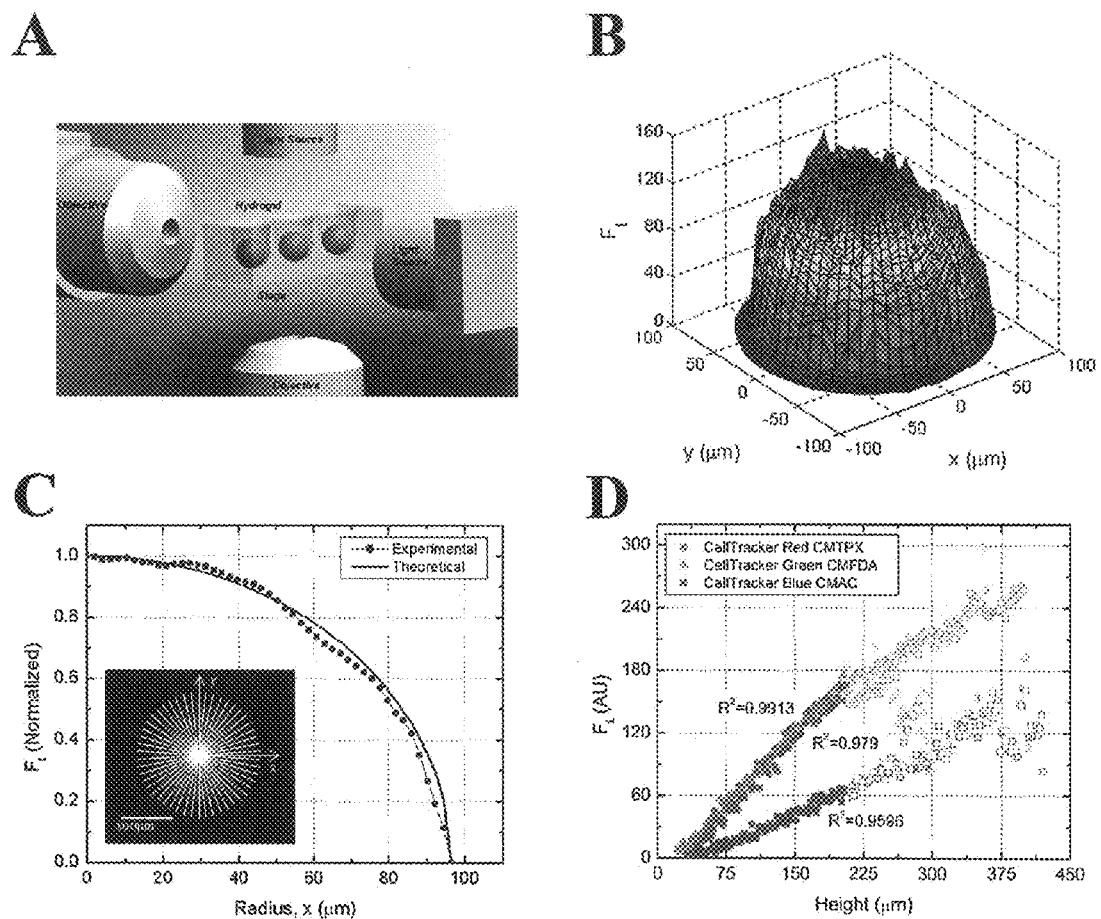
FIGS. 1A-1D: Experimental set-up to form spheroids and capture wide-field fluorescent images to quantify transport. Standard view (x, y) and side view (z) microscopy were used to obtain fluorescent images of spheroids self-assembled in a micro-molded hydrogel (A). Uniformly labeled spheroids of varying sizes were formed from cells stained with CellTracker™ green, red, or blue dyes, and fluorescent images were taken 24 hours after self-assembly. A plot of total fluorescence ($F_t(AU)$) of a single labeled spheroid as a function of x and y dimensions is shown (B). For each image, an automated MATLAB program generated fifty radial lines (inset), which were averaged to generate a single radial line (inset), which were averaged to generate a single 2D radial profile of the fluorescence intensity of one spheroid (●) compared to a theoretical profile (-) (equation 1), which calculates the total fluorescence ($F_t$ (normalized)) for each radial point (C). The height of spheroids of varying sizes that were uniformly labeled red (●), green (▲), or blue (■)were measured and plotted versus total spheroid fluorescence ($F_t(AU)$)(D). Up to a critical height ($h_c$) of about 205 μm, there is a linear relationship between spheroid height and total fluorescence, but above this height, the relationship is no longer predictable.
Figure 2:
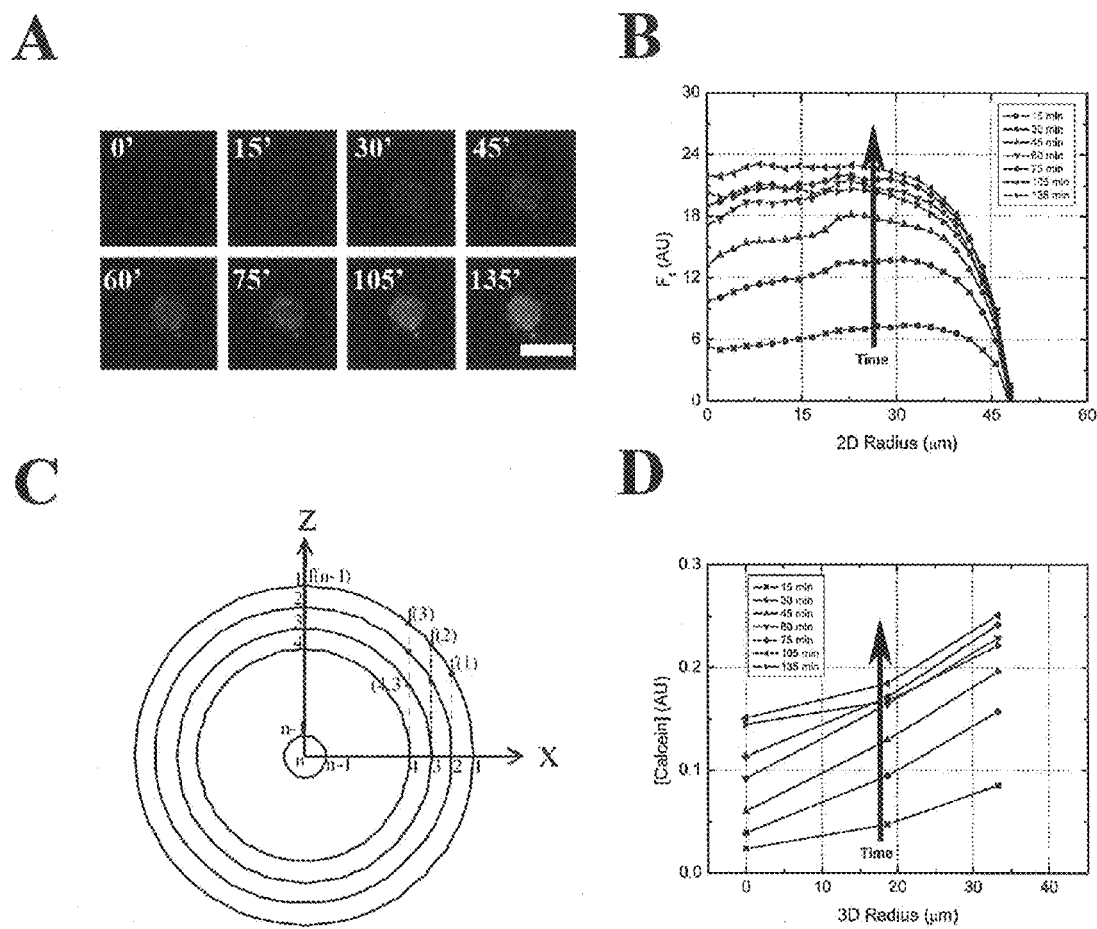
FIGS. 2A-2D: Uptake of calcein-AM, as measured by fluorescent calcein, increased with time. Spheroids of KGN cells were incubated with 1 μM calcein-AM and time-lapse fluorescent images taken over 135 minutes (A). A 2D radial profile of calcein fluorescence was generated for each time point (B). Over time, total fluorescent intensity ($F_t$ (AU)) increased and reached an approximate steady state within 75 minutes (♦). The shape of each of these radial profiles indicates that calcein concentration is highest in the outer layer of cells for all time points. To generate an average 3D radial profile of calcein concentration, the spheroid was estimated as a series of 14 μm concentric shells (multilayers) where Z is the height of the spheroid and X is the distance across the spheroid (C). The fluorescence intensity (f(1), f(2) . . . f(n−1)) is taken at 14 μm shells across X ($X_2$, $X_3$ . . . $X_n$), and the contribution from each consecutive shell is subtracted from the total fluorescence at each point $f_n$ (equation 4) to yield calcein fluorescence for each shell. A plot of calcein concentration ([Calcein] (AU)) for each concentric shell (3D radius) shows that calcein concentration is highest in the outermost cell layer, and decreases towards the core for all time points (D).

The features and other details of the invention, either as steps of the invention or as a combination of parts of the invention, will now be more particularly described and pointed out in the claims It will be understood that the particular embodiments of the invention are shown by way of illustration and not as limitations of the invention. The principle features of this invention can be employed in various embodiments without departing from the scope of the invention.

In one embodiment, the invention is a method for treating a tumor that includes screening for a selected drug that has an effect of at least one of inhibiting an efflux pump and not blocking gap junctions in tumors. The screening method includes the step of seeding a cell culture medium that includes a drug to be screened with cells in a non-adherent well to form a cell suspension. The cells are cultured to form self-assembled spheroids that have a core and an outer shell. The spheroids are incubated in the presence of a substrate of the efflux pump to thereby cause at least a portion of the substrate of the efflux pump to penetrate the cell. Uptake of the substrate and the distribution of substrate within the spheroids is imaged, whereby an increased concentration of the substrate in the outer shells of the spheroids relative to that of the total spheroids that self-assembled in the absence of the drug indicates that the drug inhibits the efflux pump, and an increase in the substrate, such as the concentration or absolute amount of the substrate, at the cores of the spheroids relative to that of spheroids that self-assembled in the absence of drug indicates that gap junction communication has not been blocked by the drug. A drug that is identified as either inhibiting an efflux pump or not blocking gap junction communication is designated a selected drug. Optionally, administration of the selected drug to a tumor is enabled, thereby treating the tumor.

In one embodiment, the method further includes combining the selected drug that is to be administered to the tumor with an anticancer drug, whereby the selected drug in the anticancer drug work in conjunction to treat the tumor.

In another embodiment, the selected drug is a drug that causes both an increase of the substrate in the outer shell of the spheroids relative to that of the total spheroids that self-assembled in the absence of the drug, and also cause an increase in the substrate, such as the concentration or absolute amount of substrate, at the cores of the spheroids relative to spheroids that self-assembled in the absence of the drug. Examples of suitable cells for culturing to form spheroids include granulosa cells, cancer cells, primary human cells, cardiomyocytes, hepatocytes, kidney cells and intestinal epithelial cells.

In another embodiment, the spheroids are pre-stained by combining the cell culture medium with a stain, and subsequently culturing the cells in a cell culture medium, whereby the resulting spheroids are stained. Examples of suitable stains include Cell Tracker™ and Cell Trace™ stains and stains that are mediated by genetically modifying the cells to express fluorescent proteins.

Typically, suitable spheroids have a height of less than about 300 µm. In another embodiment, the spheroids have a height less than about 210 µm. In still another embodiment, the spheroids have a height less than about 205 µm.

In yet another embodiment, a selected drug is one that causes a decrease in the percent or fraction of metabolized substrate at the cores of the spheroids relative to that of the total spheroids that self-assembled in the absence of the drug. Optionally, such a selected drug is administered to a tumor in combination with a facilitator of gap junction communication.

In another embodiment, the selected drug is a drug that causes a decrease in the ratio of substrate concentration in the core relative to that of the shell of the spheroids.

In yet another embodiment, the method includes the further step of combining the cell culture medium with an anticancer drug that, if the selected drug were to be administered to a tumor, the selected drug will be administered to the tumor with the anti-cancer drug. Designation of the selected drug would be dependent upon the same criteria discussed above.

Examples of tumor cells treatable by the method of the invention include ovarian cancer, breast cancer, prostrate cancer, liver cancer, renal cancer and colon cancer cells.

Methods and assays for forming microtissues and macrotissues, including spheroids, toroids and rods are described in U.S. Patent Application No: 2011/0212481, filed Oct. 1, 2010, by Morgan et al., and entitled, "Assays and Methods for Fusing Aggregates to Form Proto-Tissues," the entire teachings of which are incorporated by reference in its entirety. Methods and devices for cell aggregation and encapsulation of cells are described in WO 2007/087402, having an international filing date of Jan. 24, 2007, by Morgan et al., and entitled, "Cell Aggregation and Encapsulation Device and Methods," the entire teachings of which are incorporated by reference in its entirety.

Drug efflux transporters, or efflux pumps, such as Pgp, multi-drug resistance proteins 1-5 (ABCC1-5), and breast cancer resistance protein (BCRP or ABCG2) are well-known regulators of the absorption, distribution, and excretion of clinically important drugs and drug metabolites[4,5,7,8]. Modulation of these efflux pumps, or transporters, either intentionally via drug inhibitors or unintentionally via the side effects of certain drugs, can have profound pharmacological effects[14,18,21]. Current in vitro models based on 2D mono-layers of cells do not adequately assess these effects because they fail to replicate many of the complexities of the in vivo environment. The uptake of calcein-AM and the transport of fluorescent calcein over time in 3D multi-layer spheroids was quantified and the effects of verapamil, loperamide, and cyclosporin A, three well-known inhibitors of Pgp was tested. Although all three inhibitors increased the amount of calcein in the cells of the outer layer of the spheroid, quantification of the 3D concentration gradient showed that only cyclosporin A caused an increase of calcein in the core of the spheroid, whereas verapamil and loperamide caused a decrease by blocking gap junction communication Inhibition of gap junctions is an action not previously reported for these drugs and one that could only be determined in a 3D multilayer in vitro model.

Examples of substrates other than calcein-AM include Rhodamine 123 (Pgp), fluorescent paclitaxel (Pgp), Hoescht (BCRP—Breast Cancer Resistance Protein) and Calcein (MRP—Multidrug Resistance Protein). In the 3D assay described herein, cyclosporin A increased the concentration of calcein in both the outer layer of cells and in the core. Cyclosporin A is an immunosuppressant whose primary use is the prevention of organ rejection. Cyclosporin A and cyclosporin derivatives are inhibitors of Pgp and have also had the most clinical success in helping to combat tumor drug resistance[18]. Cyclosporin A acts by decreasing the interaction of anti-cancer drugs with the cell membrane, thereby decreasing drug efflux by Pgp[15]. The response to chemotherapy of retinoblastoma, a tumor high in Pgp expression, was improved when cyclosporin A was co-administered. Over 90% of new cases and 50% of those previously treated remained relapse-free with follow-up for 2.5 to 6 years[15,39]. However, due to its immunosuppressant activity, cyclosporin A is no longer used to inhibit Pgp. Non-immunosuppressant derivatives of cyclosporin, in particular Valspodar™, was shown to improve the uptake and retention of anticancer drugs in cancer cell lines, but no clinical benefit was observed in ovarian cancer patients treated with paclitaxel[40]. Of the three Pgp inhibitors tested, cyclosporin A was most effective at increasing both total calcein uptake and transport of calcein in our 3D multilayer system.

In contrast, verapamil and loperamide both increased the total amount of calcein in the spheroid indicating they had inhibited Pgp, but surprisingly this increase did not increase the calcein concentration in the core of spheroid. Basic diffusion principles would predict that higher concentrations in the outer layer should increase the core concentration. Verapamil is a first generation efflux pump inhibitor that functions as a competitive inhibitor of Pgp, but its primary use is to treat hypertension and angina because it blocks voltage-dependent calcium channels[41]. In fact, when tested for its ability to inhibit Pgp and enhance the action of a chemotherapeutic agent, verapamil caused cardiotoxicity[42,43]. Cardiotoxicity was reduced at lower verapamil concentrations, but these low concentrations no longer enhanced the action of the chemotherapeutic agent[18,44]. Loperamide is an opioid-receptor agonist whose primary use is the treatment of diarrhea, but it can also affect calcium levels and is a substrate for and an inhibitor of Pgp[19].

In the 3D assay described herein, the use of verapamil and loperamide resulted in uptake and transport profiles similar to those seen when gap junction communication was blocked. Treatment with the gap junction inhibitor carbenoxolone and the use of gap junction-negative cell lines (OVCAR-3 and SK-OV-3) resulted in calcein localized in the outer shell of cells and little if any calcein in the core. Thus, these data suggests that verapamil and loperamide prevent diffusion of calcein into the center of the spheroid by blocking gap junction communication between cell layers. Verapamil's inhibition of gap junctions may contribute to the cardiotoxicity observed when verapamil was tested in clinical trials as a Pgp inhibitor[42,43] Immunostaining showed that our cells expressed CX43, the same connexin expressed in cardiomyocytes.

From the 3D analysis, it can be concluded that verapamil and carbenoxolone have new previously unreported activities. Verapamil is an inhibitor of gap junctions and carbenoxolone is an inhibitor of Pgp. Furthermore, it was determined that verapamil is a more potent inhibitor of Pgp, and carbenoxolone a more potent inhibitor of gap junctions (FIGS. 9A-9F). The dose response curves suggest that verapamil's mechanism of action on gap junctions may be similar to its action on Pgp. While the dose response curves for carbenoxolone suggest that it may block Pgp by a different mechanism than it blocks gap junctions.

For many years, it has been recognized that 3D in vitro models are superior to 2D models because they more accurately replicate the phenotype of cancer cells as well as the complex tumor microenvironment[45]. Cancer cells grown in 3D are far more resistant to treatment with radiation and chemotherapy than cells grown in 2D and so are thought to be more similar to tumors in vivo[3]. This effect has been shown for cancer cells grown using several different 3D systems, including tumor spheroids grown from single cells in gels and cancer cells grown on various scaffolds. Quantitative transport data was obtained from the system described herein because the multi-cellular tumor spheroids are self-assembled within about 24 hours without added scaffold or extracellular matrix proteins; multi-layers are formed that maximize cell-to-cell contact and cell-to-cell communication. The uniformity and radial symmetry of the spheroids and their location on the same optical plane enabled us to obtain a time series of fluorescent images and to develop a mathematical model of the 3D gradient of calcein with respect to each of the layers of the spheroid. Due to the 3D analysis used in our assay, the effectiveness of a Pgp inhibitor was determined by measuring the increase in total calcein in a spheroid. With the same data set, it was also possible to determine if a Pgp inhibitor alters transport through gap junctions by measuring the change in compartmentalization of calcein within the spheroid.

These transport studies could easily be extended to other cell types. Numerous cell types, including cancer cells and primary human cells will self-assemble 3D spheroids in this system[46,47]. Examples of suitable cells include C6 glioblastoma cells, CaCo-2 colon cancer cells, MCF-7 breast cancer cells, HEK-293 human embryonic kidney cells, any primary tumor cells, primary hepatocytes, endothelial cells and fibroblasts.

Moreover, even mixtures of two different cell types will self-assemble into spheroids and often self-sort during self-assembly with one cell type forming the inner core and the other cell type forming the outer coating[48]. It may be possible to perform 3D in vitro transport studies using spheroids that replicate the heterotypic cell interactions seen in major barriers to drug transport such as the blood brain barrier. Quantitative 3D models may be useful for discovering new more effective inhibitors of drug efflux transporters (Pgp, ABCC (also known as MRP), BCRP) and may also be helpful in the early identification of possible side effects and drug-drug interactions of new drug candidates. Multidrug resistance protein family of ATP-dependent efflux pumps (ABCC1-ABCC6, formerly MRP1-MRP6) may also be helpful in the early identification of possible side effects and drug-drug interactions of new drug candidates.

The following examples illustrate embodiments of the invention and are not intended to be limiting in any way.

Exemplification

As described herein, the effects of Pgp inhibitors using the calcein-AM efflux assay in a multi-layer 3D spheroid model were studied. Using wide field fluorescent images and quantitative image analysis, we have calculated the uptake, efflux, and penetration of calcein-AM and its fluorescent derivative, calcein, in the presence of well-known inhibitors of Pgp (verapamil, loperamide, and cyclosporin A). We found that although all three inhibitors were effective in increasing the concentration of calcein in the outermost layer of cells in a multi-layer spheroid, our new 3D positional analysis revealed that only cyclosporin A increased the concentration of calcein in the core of the multi-layer spheroid. Verapamil and loperamide inhibited the transport of calcein into the core, similar to the uptake and transport observed when we blocked gap junction communication via carbenoxolone treatment or when we tested cell lines lacking functional gap junctions. In addition to identifying previously unreported actions of verapamil and loperamide (inhibition of gap junctions), these results describe a method amenable to high throughput screening and demonstrate the importance of using a more realistic multi-layer 3D model to evaluate inhibitors of Pgp.

Materials and Methods

Design, Fabrication, and Casting of Micro-Molds Micromolds used to form hydrogels for forming spheroids were designed using computer design software (SolidWorks Corporation, Concord, Mass.)[27,28]. Designs used for side-view microscopy contained a single row of 21 recesses with rounded bottoms, each recess about 400 μm in diameter and about 800 μm in depth. Wax molds were produced with a ThermoJet® rapid prototyping machine (3D Systems Corporation, Valencia, Calif.). Polyacrylamide gels were cast from the wax molds. All chemicals were purchased from Sigma Aldrich (St. Louis, Mo.). A mixture of acrylamide/bis-acrylamide (29:1 ratio), ammonium persulfate (APS), 0.5 M Tris buffer (pH 6.8), and Dulbecco's modified Eagle's medium (DMEM) (Invitrogen, Carlsbad, Calif.) was degassed. N,N,N',N'-tetramethylethlyenediamine (TEMED) was added to initiate polymerization. The solution was pipetted into the wax mold and covered with a cover slip to create a flat bottom on the gel. After 10 minutes, the hydrogel was removed from the mold, washed several times with DMEM, and incubated overnight in DMEM.

Cell Culture and Spheroid Formation

KGN cells, a human granulosa cell line, were grown in DMEM[29]. OVCAR-3 and SK-OV-3 cells were grown in Roswell Park Memorial Institute medium (RPMI; Invitrogen). Both media were supplemented with 10% fetal bovine serum (FBS) (Thermo Fisher Scientific, Waltham, Mass.) and 1% penicillin/streptomycin and grown at 37° C. and 10% $CO_2$. Cells were trypsinized using 0.05% trypsin and resuspended to the desired cell concentration. Spheroids that were pre-stained were formed from cells incubated with 5 μM CellTracker™ Red CMPTX, CellTracker™ Green CMFDA, or CellTracker™ Blue CMAC (Invitrogen) in serum-free DMEM for 1 hour prior to trypsinization. 75 μl of the cell suspension was pipetted into the seeding chamber of each gel. Cells were allowed to settle for 20 minutes and 4 mL of medium was added. Cells self-assembled for 24 hours to form spheroids before experimentation.

Microscopy

Horizontal view microscopy was used to measure the height (z) of the spheroid from a Mitutouo FS-110 microscope altered to lie on its back. Samples were placed on a translational stage and brightfield images were taken through the eyepiece using a Nikon Coolpix 900 camera. For standard, x-y view images, a Carl Zeiss Axio Observer Z1 equipped with an AxioCam MRm camera (Carl Zeiss MicroImaging, Thornwood, N.Y.), an Xcite 120 XL mercury lamp (Exfo Life Sciences Division, Mississauga, Ontario), and an incubation chamber (37° C., 10% $CO_2$) was used to obtain brightfield, phase contrast, and epi-fluorescent images.

Image Analysis

Quantitative image analysis was performed using a custom MATLAB (Mathworks, Natick, Mass.) program. Briefly, fifty evenly spaced radii were drawn across each spheroid and fluorescence at each pixel was averaged. Background fluorescence outside the spheroid was subtracted, taking into account that the fluorescence surrounding the spheroids decreased exponentially and was thus different for different points within the spheroid. Total spheroid fluorescence was determined by the integration of the fluorescent profiles (Equation 2). To compare data across experiments, we normalized the spheroids to the fluorescence per depth of single cells at the final time point.

The height (h) at each point in the spheroid was calculated using the formula for an ellipse with half-width a and half-height b, such that:

$$h(x) = b\sqrt{1 - \left(\frac{x}{a}\right)^2} \qquad \text{Equation (1)}$$

The fluorescent intensity at each height was averaged over all spheroids stained with CellTracker™ dyes [red (n=52), green (n=74), and blue (n=60)]. The total fluorescence at each point is the integrated fluorescence of all cells below it, expressed as:

$$F_t(x) = \int_0^{h(x)} C(x, z)\alpha p^2 \, dz \qquad \text{Equation (2)}$$

where $C(x, z)$ is the concentration of the fluorophore along the y=0 plane, α is the emitted fluorescence per mole of fluorophore, and p is the resolution of one pixel (2 μm×2 μm). The uniformly pre-stained spheroids have constant fluorophore concentration, $C_o$. The above integral shows that the total fluorescence is linearly related to the height of the spheroid below each point:

$$F_t = C_o \alpha p^2 h \qquad \text{Equation (3)}$$

Uptake of Calcein-AM and Transport of Calcein

To measure uptake of calcein-AM and transport of calcein, medium was removed from the hydrogels containing self-assembled KGN spheroids (24 hours), and replaced with serum-free DMEM containing 1 μM calcein-AM (Invitrogen). Fluorescent imaging of calcein began immediately and images were taken at regular intervals over 135 minutes at 37° C. and 10% $CO_2$. To measure loss or loss of calcein, hydrogels containing KGN spheroids that had been incubated with calcein-AM for 135 minutes, thus loading the spheroids with calcein, were rinsed with DMEM and incubated in DMEM without calcein-AM. Images were taken once per hour for 11 hours, at 37° C. and 10% $CO_2$.

Drug Treatment to Block P-Glycoprotein and Gap Junctions

Stock solutions of verapamil monohydrochloride hydrate, loperamide hydrochloride, and cyclosporin A (Sigma) (5 μg/ml, 100 μM, and 25 μM, respectively) were used to make working solutions in serum-free DMEM. Hydrogels were equilibrated with a drug-containing medium overnight at 37° C. and 10% $CO_2$, and spheroids were self-assembled for 24 hours in their respective drug concentration. At these drug concentrations, self-assembly kinetics were unaltered. A working solution of carbenoxolone (Sigma) was prepared by diluting appropriate volumes of a 10 mM stock solution into serum-free medium. Spheroids were assembled for 24 hours and then pretreated with carbenoxolone for 5 hours prior to adding calcein-AM for the uptake assay. Medium containing drug and calcein-AM were used for the uptake assay.

Immunohistochemistry and Confocal Microscopy

Twenty hours after self-assembly, spheroids were fixed with 4% paraformaldehyde (Fisher) overnight in phosphate-buffered saline (PBS) and blocked and permeabilized for two hours with 10% goat serum (Jackson Immuno Research Laboratories, West Grove, Pa.), 1% bovine serum albumin (Sigma), and 0.5% Triton X-100 (VWR, West Chester, Pa.). To visualize p-glycoprotein and gap junctions (CX43), spheroids were incubated with a mouse monoclonal anti-p-glycoprotein antibody and a rabbit polyclonal anti-Connexin 43/ GJA1 antibody (1:500, Abcam, Inc., Cambridge, Mass., USA) at room temperature for two hours and at 4° C. overnight. Spheroids were brought to room temperature for two hours and rinsed with 0.5% Triton X-100 in PBS. Cy3-conjugated goat anti-mouse secondary antibody and Cy2-conjugated goat anti-rabbit secondary antibody (1:200, Jackson Immuno Research Laboratories) were applied at room temperature for two hours followed by 4° C. overnight. Spheroids were washed three times with 0.5% Triton X-100 in PBS. Nuclei were visualized by 4',6-diamidino-2-phenylindole (DAPI) counter-staining. Immunostained spheroids were transferred to glass-bottom confocal dishes (Menzel-Glaser, Braunschweig, Germany) and were visualized using a Zeiss LSM 510 META confocal microscope (Carl Zeiss Microscopy, N.Y., USA).

Statistical Analysis

Two experimental groups were tested for significant variability between sample means using analysis of variance (ANOVA). If significant differences were established, we performed a Bonferroni t-test to determine significance.

RESULTS

Determining the Critical Height for Imaging Spheroids

To quantify the transport of fluorescent molecules into spheroids using wide field fluorescence, we formed spheroids of controlled size and obtained images of their x-, y-, and z-dimensions (FIGS. 1A-1D). Mono-dispersed KGN cells were seeded onto a micro-molded non-adhesive hydrogel gel whereon they self-assembled spheroids after 24 hours. To determine the detection limits of different fluorophores, wide-field fluorescent images were obtained of spheroids formed from cells that were stained with one of three dyes (CellTracker™ Red CMTPX, CellTracker™ Green CMFDA, or CellTracker™ Blue CMAC). For each image, fifty radial lines were generated using a MATLAB algorithm and averaged to generate a single 2D radial profile of fluorescence intensity. The 2D radial profile for these uniformly stained spheroids was parabolic and consistent with the predicted theoretical profiles (Equation 1). Total fluorescence intensity for spheroids of varying sizes showed a linear relationship between spheroid height and fluorescence for all three fluorophores up to a critical spheroid height of about 205 µm, implying that for spheroids about 205 µm and smaller, 100% of the emitted fluorescent light (red, blue, green) was captured. For spheroid heights greater than about 205 the relationship was no longer linear for the green and red fluorophores, but was linear for the blue fluorophore up to a height of about 250 µm.

Multi-layer Uptake and Transport by Spheroids

To measure uptake and transport, spheroids were incubated with calcein-AM (1 µM) and images of fluorescent calcein were taken every fifteen minutes for about 135 minutes (FIGS. 2A-2D). Calcein fluorescence in the spheroid increased rapidly over time, and the time series of 2D radial profiles showed that fluorescence increased throughout the 135 minutes. However, none of the 2D radial profiles attained the full parabolic curve seen with uniformly stained spheroids. Maximum calcein fluorescence was not in the center of the spheroid (point of greatest cell number), rather, it was located near the outer edge of the spheroid. This indicated that as uptake (calcein-AM) and transport (calcein) occurred over time, the highest concentration of calcein was in the outer layer of the spheroid and calcein concentration decreased towards the spheroid core.

Figure 3:
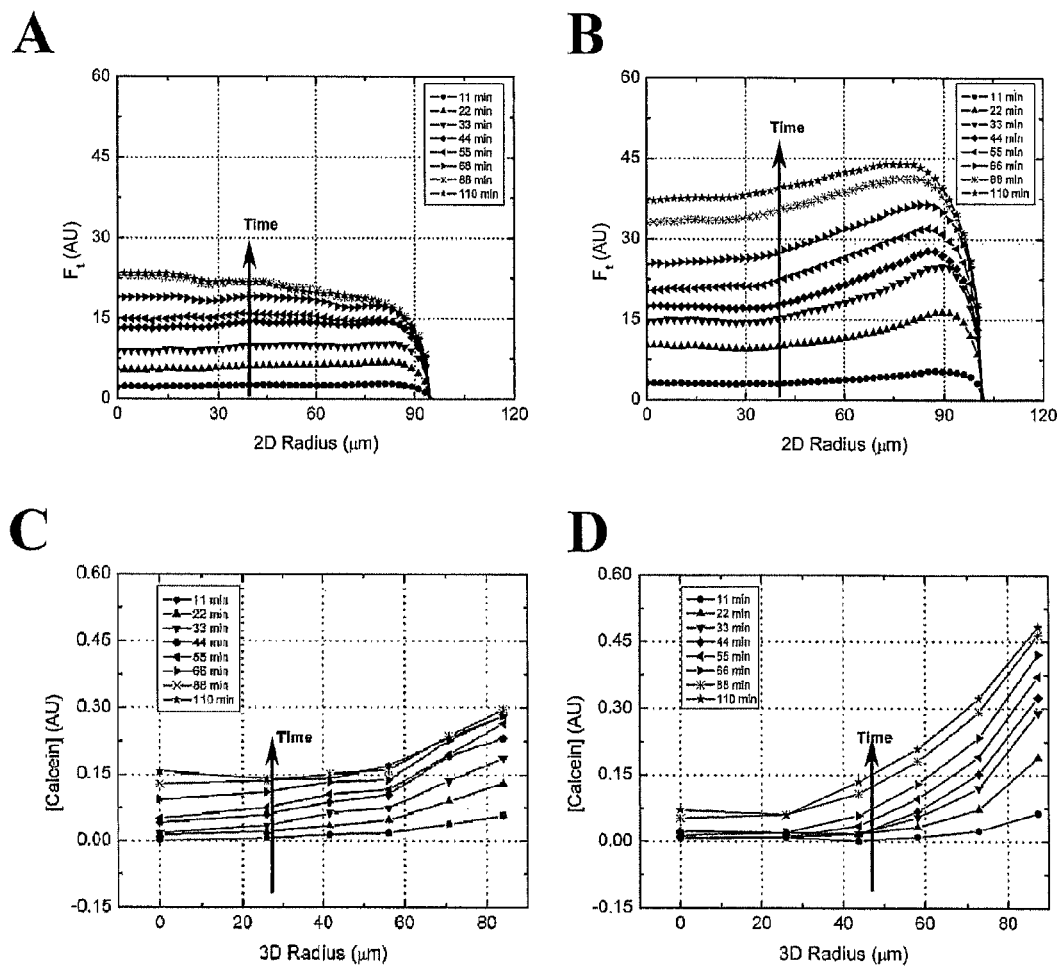
FIGS. 3A-3D: Verapamil increases total spheroid calcein, but decreases transport of calcein. Spheroids were incubated with 1 μM calcein-AM in the presence of verapamil (untreated, A, C), (25 μM, B, D), and images were taken every 11 minutes for 110 minutes. A time series of 2D radial profiles (A, B) shows that total fluorescence of all spheroids ($F_t$ (AU)) increase with time. Verapamil treatment increases total spheroid fluorescence over untreated controls, but fluorescence is preferentially located in the outermost layer of cells. The quantitative 3D radial profiles of calcein concentration ([Calcein] (AU))(C, D) reveal that although verapamil increases uptake in the outer layer over control (every time point), calcein concentration at the center of the spheroid does not increase.

To deconvolve this fluorescent signal into an average 3D radial profile, the spheroid was estimated as a series of concentric spheres (multi-layers). Each layer (shell) was 14 µm in width and contained a homogenous concentration of fluorescent calcein (FIGS. 3C and D). The total fluorescence $f(i)$ at X, layer is sum of the fluorescence contribution from all shells at $X_i$. Mathematically, the total fluorescence can be written as $$f(i) = 2\sum_{j=1}^{i} f_{norm}(j)[h(i+1, j) - h(i+1, j+1)] \qquad \text{Equation (4)}$$

Here, $f_{norm}(j)$ is the fluorescence/height in the $i^{th}$ shell and $h(i, j)$ is the height at point $(X_i, Y_j)$. Note $h(i, i)=0$ lies at the centerline of the spheroid. Hence, we can determine $f_{norm}(i)$ can be determined by sequentially subtracting the fluorescence due to inner shells from the total fluorescence $f(i)$ at $X_i$. Equation (4) results in the following iterative formula:

$$f_{norm}(i) = \frac{1}{h(i+1, i)}\left[\frac{f(i)}{2} - \sum_{j=1}^{i-1} f_{norm}(j)[h(i+1, j) - h(i+1, j+1)]\right] \qquad \text{Equation (5)}$$

This analysis was used to plot calcein concentration as a function of 3D radius. The inner core was taken as about ≥14 µm from the center in the smallest dimension to ensure the core contained whole cells. Even at later time points, the concentration of calcein in the core did not reach the same concentration as the outer shell, indicative of cellular barriers to transport.

Multi-layer Uptake and Transport in the Presence of P-Glycoprotein Inhibitors To determine the effects of a Pgp inhibitor on the uptake of calcein-AM and transport of calcein, the assay was performed in the presence of verapamil (FIGS. 3A-3D). The time series of 2D radial profiles showed that total spheroid fluorescence increased with verapamil treatment, consistent with inhibition of Pgp. However, the shape of the 2D radial profiles of verapamil-treated samples (FIG. 3A) was different from untreated controls (FIG. 3B). Fluorescence of the outer layer versus the core was increased indicating more calcein in the outer layer of the drug-treated samples. Three dimensional (3D) analysis showed that, in addition to increasing the total calcein in a spheroid, verapamil treatment altered the concentration gradient within the spheroid (FIG. 3D). Calcein concentration was increased in the outer layer, as would be expected by inhibition of the Pgp, but calcein concentration was not elevated in the core as a result of the increased levels in the outer layer. High levels of calcein in the outer layer should lead to increased levels in the core, but surprisingly, our 3D analysis showed that calcein levels in the core were higher in untreated samples (FIG. 3C) than in those treated with verapamil (FIG. 3D).

Figure 4:
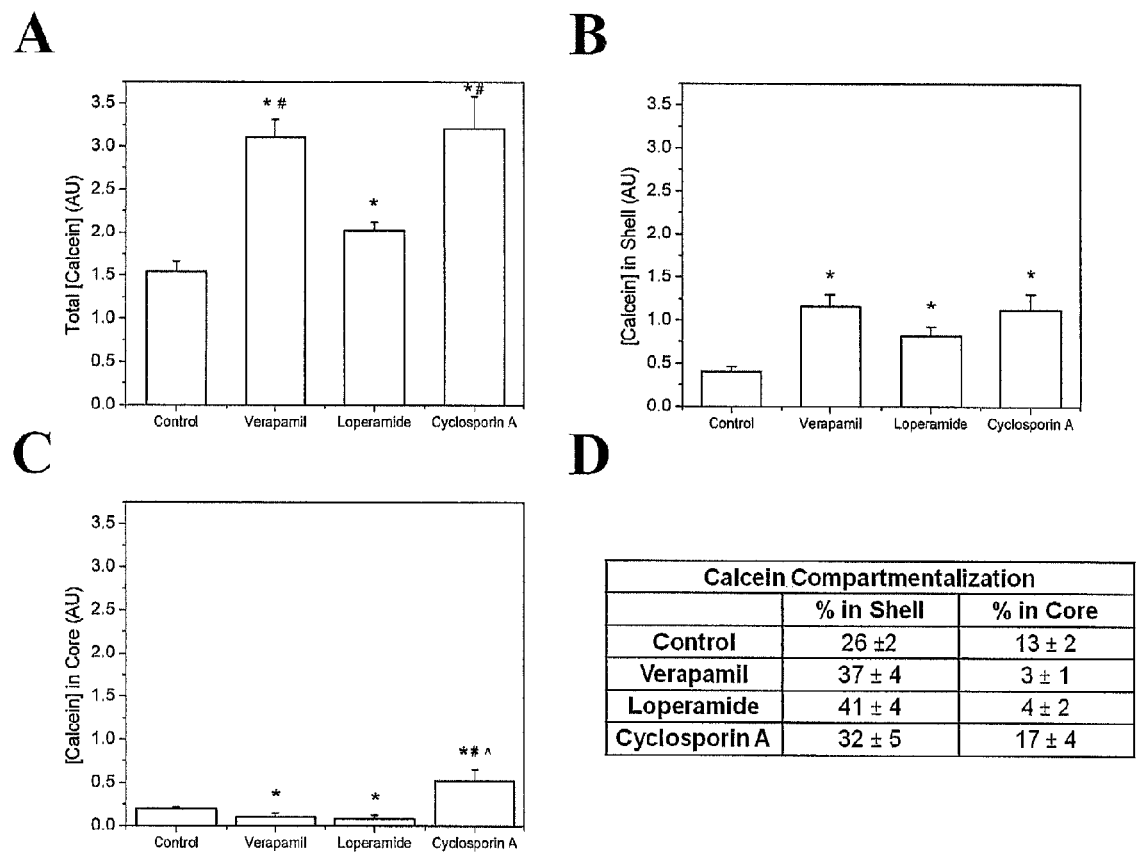
FIGS. 4A-4D: Cyclosporin A increases total spheroid calcein and more calcein is transported to the core. Spheroids were incubated with 1 μM calcein-AM in the presence of verapamil, loperamide or cyclosporin A. The quantitative 3D radial profiles were used to determine (A) the total calcein concentration ([Calcein] (AU)), (B) calcein concentration in the outer layer of cells and (C) calcein concentration in the inner core of the spheroid at 110 minutes. ANOVA found differences within the groups and a Bonferroni t-test showed the calcein concentration in the total spheroids as well as in the outer layer of spheroids treated with 5 μM loperamide, 25 μM cyclosporin A, and 25 μM verapamil were significantly higher than controls. However, only spheroids treated with 25 μM cyclosporin A had a higher concentration of calcein in the spheroid core. (*$p<0.01$ compared to controls, #$p<0.01$ compared to loperamide, ^$p<0.01$ compared to verapamil). To quantify calcein compartmentalization, we normalized the data and calculated the percentage of total calcein in the outer shell and the core (D). Verapamil and loperamide decreased the percentage of calcein in the core, whereas calcein compartmentalization was unaffected by cyclosporin A treatment, indicating no block to calcein transport (n=15).

To determine if other inhibitors of Pgp had similar effects, loperamide and cyclosporin A were tested and the 3D analysis was employed to quantify calcein in the outer shell and the core (FIGS. 4A-4D). The total concentration of calcein in the spheroids treated with loperamide (5 µM), cyclosporin A (25 µM) and verapamil (25 µM) was significantly increased compared to untreated controls, and calcein was significantly increased in the outer shell. However, only treatment with cyclosporin A caused a significant increase in calcein in the core of the spheroid versus the core of untreated samples (FIG. 4C). To determine if transport of calcein from the outer layer to the core was actively inhibited by any of the Pgp inhibitors, we calculated the core/shell ratio of calcein concentrations and compared these to untreated samples. No change to the ratio would imply that the transport of calcein from the outer shell to the inner core was unaffected, whereas a decrease in the ratio would suggest a block to transport. When compared to untreated controls, the core/shell ratios decreased by 63±6% for 5 µM loperamide and by 48±4% for 25 µM verapamil, but not for 25 µM cyclosporin A. To account for differences in total spheroid calcein levels, we normalized the data and determined the percentage of calcein in the outer shell versus the core. This compartmentalization of calcein in the spheroids was altered in each of the treated samples. In verapamil and loperamide treated samples, the percentage of calcein in the outer most shell was increased compared to control, while the percentage of calcein in the core was decreased. After treatment with cyclosporin A, calcein concentration increased in all compartments, such that the percentage of calcein in the shell and core compartments were not significantly different from their respective compartments in untreated samples. This indicated that cyclosporin A did not alter transport of calcein between layers.

Multi-layer Uptake and Transport while Inhibiting Gap Junctions

Figure 5:
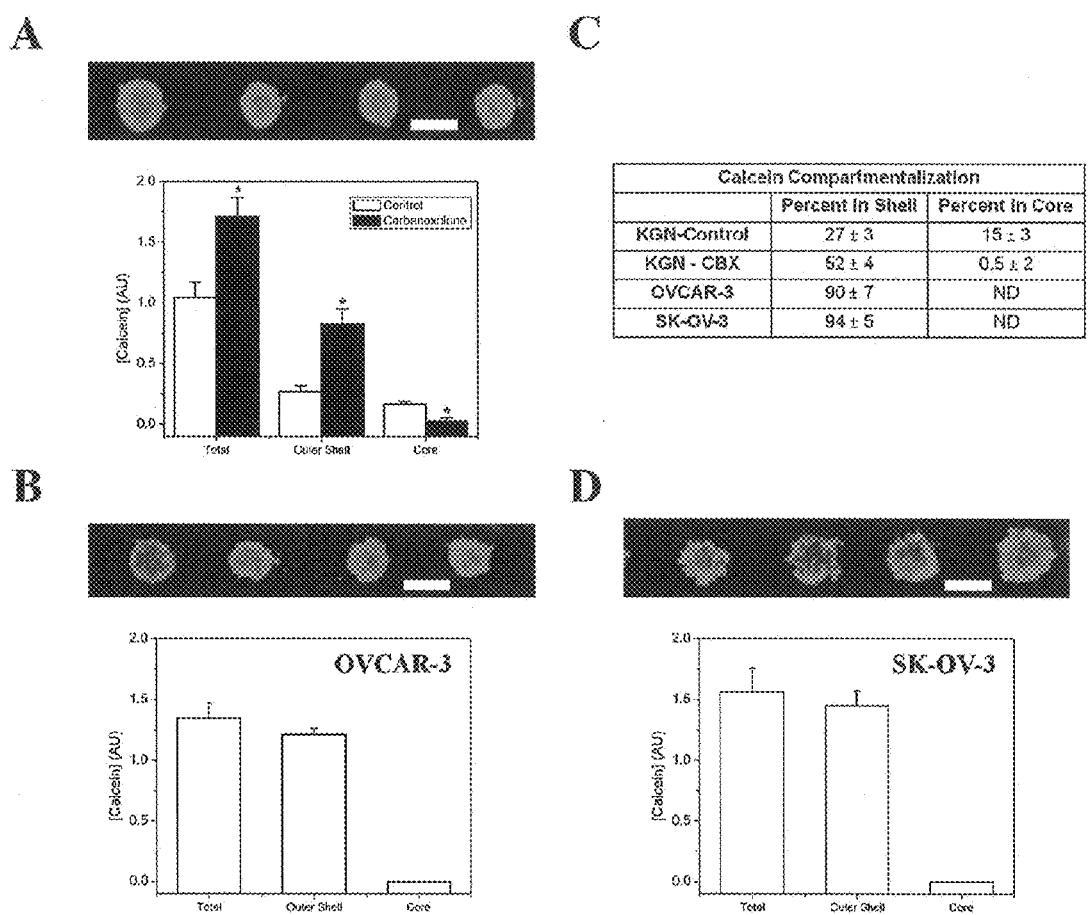
FIGS. 5A-5D: Gap junctions control calcein transport between the multi-layers. (A) KGN spheroids were incubated with 1 μM calcein-AM in the presence CBX (100 μM), a gap junction inhibitor. Compared to untreated controls, total spheroid calcein as well as calcein in the outer shell of CBX treated spheroids were increased after 135 minutes (*$p<0.001$). Conversely, calcein in the core of CBX treated spheroids was decreased compared to control (*$p<0.001$). The increase in total spheroid calcein with CBX treatment was unexpected since CBX is thought to be predominately a gap junction inhibitor. To more accurately quantify CBX effects on gap junctions, we normalized the data and quantified the percentage of calcein present in the outer shell versus the core (B) (n=18). This compartmentalization analysis showed that CBX treatment inhibited transport of calcein into the core. Ovarian cancer cell lines, OVCAR-3 (C) and SK-OV-3(D), lacking functional gap junctions were incubated with 1 μM calcein-AM and calcein distribution was quantified from fluorescent images at 75 minutes. Calcein was localized predominately to the outer shell of OVCAR-3 and SK-OV-3 spheroids. The compartmentalization analysis showed that calcein transport to the core was not detectable. The scale bar is 200 microns.

To determine if the decrease in calcein transport mediated by verapamil and loperamide might be due to inhibition of gap junctions, we tested the effects of carbenoxolone (CBX) (FIG. 5A). Compared to untreated controls, CBX treatment increased the total amount of calcein in the entire spheroid. Calcein in the outer shell of CBX-treated samples was 3-fold higher than controls, and calcein in the core of CBX-treated samples was 8-fold less. The percentage of calcein in the outer shell increased from 27±3% to 52±4% with CBX treatment, whereas the percentage of calcein in the core decreased from 15±3% to 0.5±2% with CBX treatment. Two NCI-60 ovarian cancer cell lines, OVCAR-3 (FIG. 5C) and SK-OV-3 (FIG. 5D), which do not express functional gap junctions were also tested. Transport of calcein into the core of OVCAR-3 and SK-OV-3 spheroids was negligible. The majority of calcein was confined to the outermost layer, which contained 91±7% and 94±7% of the total calcein of OVCAR-3 and SK-OV-3 spheroids, respectively (FIG. 5B).

Verapamil and Carbenoxolone Target both Pgp and Gap Junctions

Figure 6:
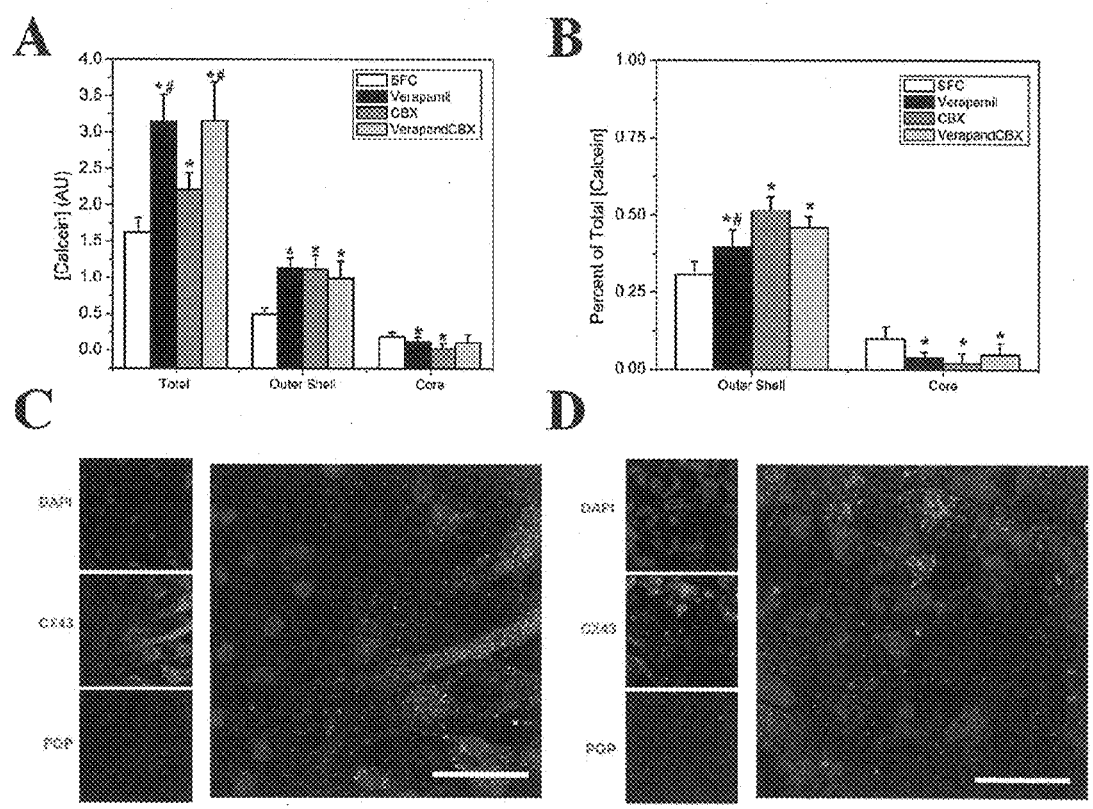
FIGS. 6A-6D: Verapamil and CBX inhibit both Pgp and gap junctions. KGN spheroids were incubated with 1 μM calcein-AM in the presence of verapamil alone, CBX alone, or verapamil plus CBX for 75 minutes. Calcein concentration was measured in the entire spheroid, the outer shell, and the inner core (A). As expected, verapamil's inhibition of Pgp resulted in an increase in total spheroid calcein versus untreated spheroids. Likewise, CBX treatment also increased total spheroid calcein suggesting that it also inhibits Pgp, although not to the same extent as verapamil. Levels of total spheroid calcein were increased with verapamil plus CBX treatment, but no greater than treatment with verapamil alone. This suggests that CBX does not target an efflux pump different from Pgp. To quantify the effects of verapamil and CBX on gap junctions, we normalized the data and quantified the percentage of calcein present in the outer shell versus the core (B). As expected, CBX inhibition of gap junctions resulted in an increase in the percentage of calcein in the outer shell versus the core. Likewise, verapamil treatment increased the percentage of calcein in the shell versus the core, but not to the same extent as CBX. The percentage of calcein in the outer shell versus the core for samples treated with verapamil plus CBX were increased, but were no greater than treatment with CBX alone. This suggests that verapamil does not target a gap junction different from the one targeted by CBX. KGN cells grown in 2D and spheroids immuno-stained for Pgp and gap junctions (connexin 43, CX43) were visualized using confocal microscopy (C). KGN cells and KGN spheroids stained positive for Pgp (green) and CX43 (red), but these proteins were not co-localized (D). DAPI (blue) staining is provided as a reference for cell location. 40× with an additional 3× zoom, scale bar=50 μm (n=15).
Figure 7:
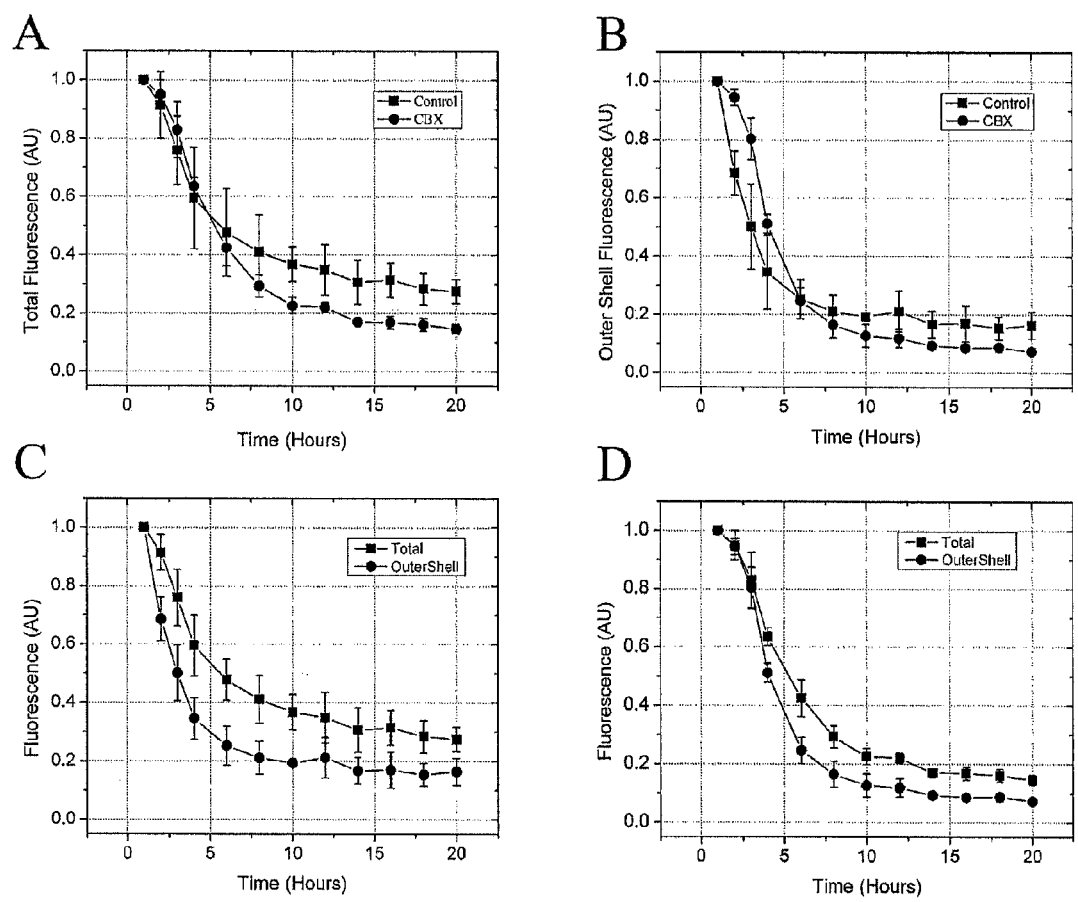
FIGS. 7A-7D: Carbenoxolone slows loss of calcein from the outer shell. KGN spheroids with and without carbenoxolone treatment were incubated with 1 μM calcein-AM for 135 minutes. Calcein-AM was then removed and replaced with drug-free medium. Images were taken once per hour for 20 hours to determine the rate of calcein loss and data normalized to the initial fluorescence. Loss from the entire spheroid was measured by the total spheroid fluorescence and decreased at the same initial rate for control and carbenoxolone treated spheroids (A). After 10 hours, carbenoxolone treated spheroids had lost more calcein than controls. When we analyzed loss from the outer shells only, carbenoxolone significantly slowed the initial rate versus control (13±1% versus 17±3% per hour, $p<0.05$) (B). A comparison of calcein initial loss rates from the outer shell versus the entire spheroid for controls showed that loss was greater from the outer shell versus the entire spheroid control (10±2% versus 14±2% per hour, $p<0.05$) (C). When treated with carbenoxolone, loss from the outer shell decreased and was similar to loss from the entire spheroid (D).

To determine if CBX might also inhibit Pgp, we quantified calcein in KGN spheroids treated with both CBX and verapamil (FIGS. 6A-6D). Compared to untreated controls, total calcein in the entire spheroid was increased for spheroids treated with verapamil alone (2-fold) and CBX alone (1.5-fold). In samples treated with verapamil plus CBX, the increase in total calcein uptake was also 2-fold and was no different from samples treated with verapamil alone (FIG. 6A). This suggests that CBX increases total spheroid calcein by also inhibiting Pgp. When calcein loss over time was measured, CBX slowed the initial rate of loss from the outer shell (17±3% versus 13±1% per hour, $p<0.05$), but had no effect on total spheroid calcein. The difference in loss rates from the outer shell was not enough to account for the CBX mediated increase in calcein (outer shell or entire spheroid) over 135 minutes (FIGS. 7A-7D).

Figure 8:
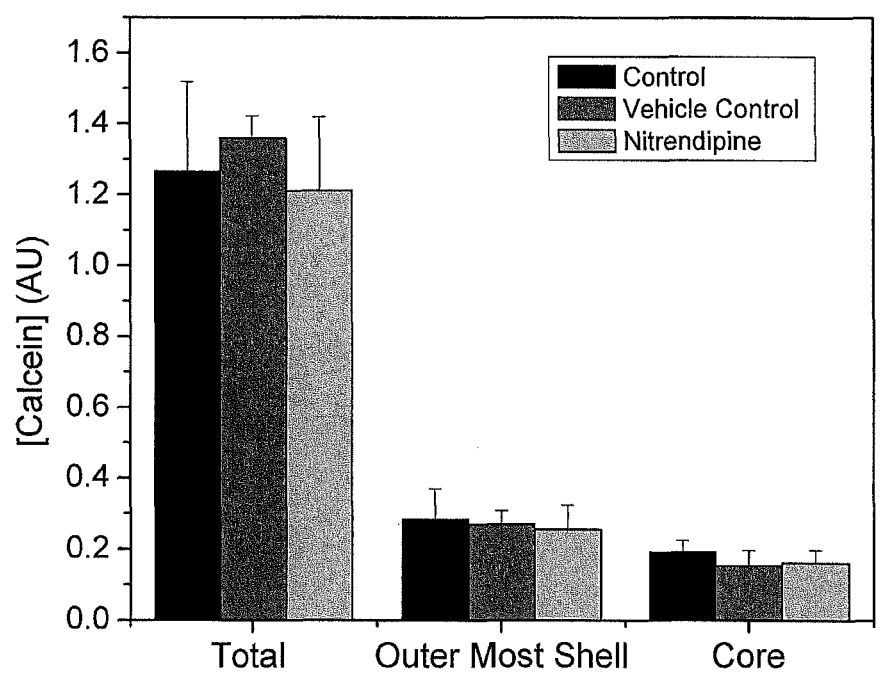
FIG. 8: Blocking L-type calcium channels with nitrendipine does not change the uptake of calcein-AM, nor the transport of calcein. KGN spheroids treated with 10 μm nitrendipine for 3 hours to irreversibly block calcium channels were incubated with 1 μM calcein-AM for 75 minutes. There was no statistical difference in calcein levels in the entire spheroid for untreated, vehicle control (DMSO) and drug treated spheroids. Likewise, calcein levels were the same in the outer shell and the core of the spheroids. Thus, the effects of verapamil and loperamide on calcein uptake and transport are not mediated via calcium channel blocking activity.
Figure 9:
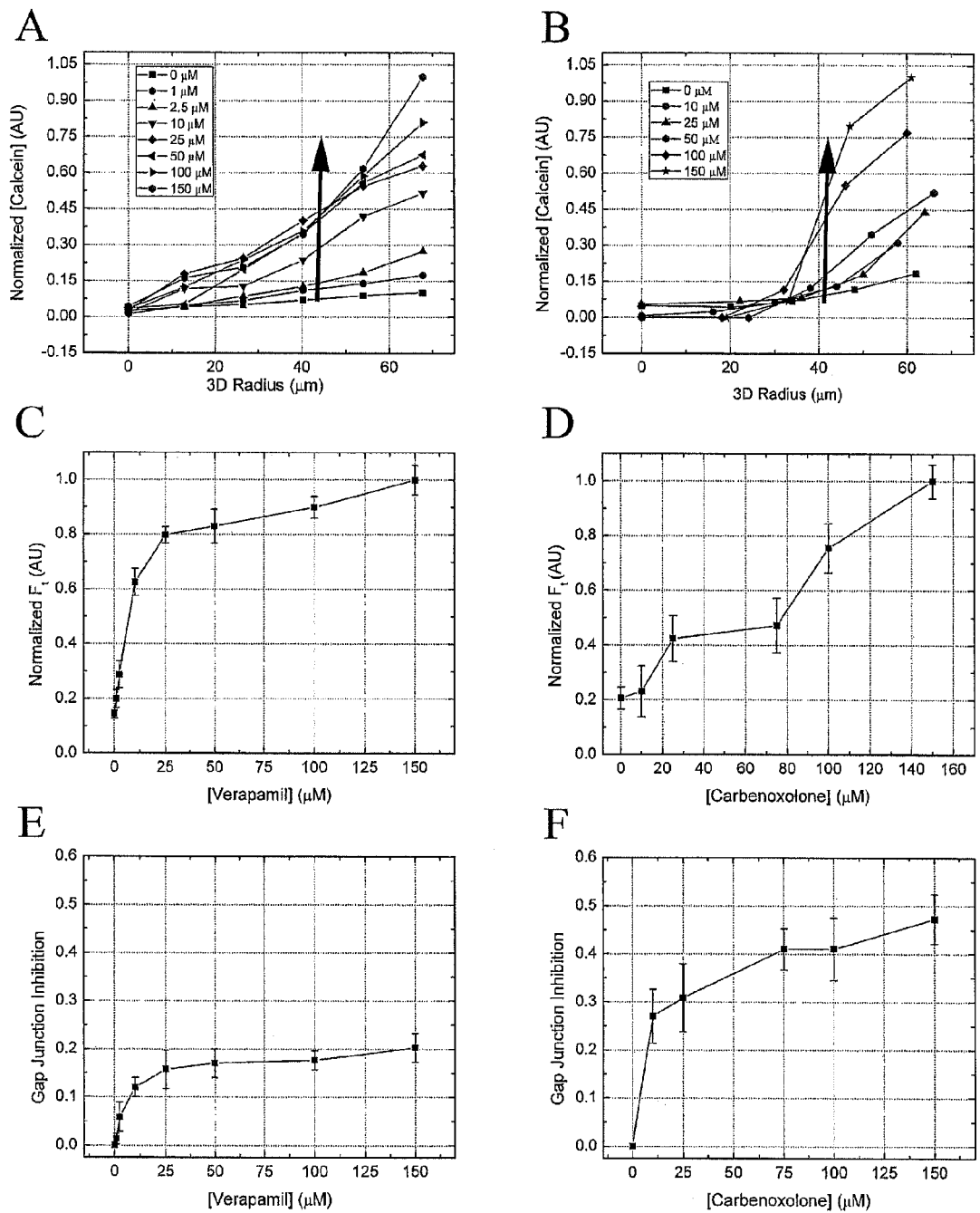
FIGS. 9A-9F: Dose response of verapamil and carbenoxolone with regards to Pgp and gap junction activities. KGN spheroids were incubated with 1 μM calcein-AM in the presence of varying doses of verapamil (A, C, E) or carbenoxolone (B, D, F) and fluorescent images obtained after 75 minutes. The 3D radial profiles of drug treated spheroids (A, B) revealed that increasing concentrations of verapamil and carbenoxolone both resulted in increased calcein uptake, but that calcein was more localized to the outer shell with carbenoxolone treatment. To determine dose response with respect to inhibition of Pgp (C, D) we plotted total calcein uptake by spheroids (n=15) as a function of drug concentration. To aid comparison, the data was normalized to the highest point. For verapamil, half-maximal response was 8.5 μM, whereas for carbenoxolone half-maximal response was 81 μM. There was a linear dose response for carbenoxolone versus verapamil which rose rapidly and reached a plateau. To determine dose response with respect to inhibition of gap junctions (E, F), the ability of a drug to increase the fraction of calcein compartmentalized to the outer shell was calculated. If the fraction of calcein was the same as the untreated control this was zero percent inhibition. If all calcein was confined to the outer shell this was 100% inhibition. For verapamil, half-maximal response was 8.6 µM similar to the concentration that elicited half-maximal inhibition of Pgp. For carbenoxolone, half-maximal response for gap junction inhibition was 9.4 µM, significantly lower than the concentration that elicited half-maximal inhibition of Pgp. When comparing the maximal responses, carbenoxolone inhibited gap junctions to a greater extent than verapamil.

To determine if verapamil might also inhibit gap junctions, we quantified calcein compartmentalization. Compared to controls, the percentage of calcein in the outer shell was increased for samples treated with verapamil alone, CBX alone, and verapamil plus CBX. Verapamil plus CBX was no different from CBX alone. Likewise, compared to controls, the percentage of calcein in the core was reduced for samples treated with verapamil alone, CBX alone, and verapamil plus CBX. Verapamil plus CBX was no different from CBX alone. These data suggest that verapamil also inhibits gap junctions. To rule out the possibility that this effect was mediated by verapamil's calcium channel-blocking activity and mediated via a change in intracellular calcium, we tested nitrendipine, a highly-specific calcium channel blocker. Nitridipine had no effect on total spheroid calcein nor calcein compartmentalization (FIG. 8). KGN cells cultured in 2D and 3D spheroids were immuno-stained for Pgp and connexin 43 (CX43). Both were positive for both proteins, and the Pgp and CX43 signals did not co-localize (FIGS. 6C and 6D).

While this invention has been particularly shown and described with references to example embodiments thereof, it will be understood by those skilled in the art that various changes in form and details may be made therein without departing from the scope of the invention encompassed by the appended claims.

REFERENCES

1 Jang, S. H., Wientjes, M. G., Lu, D. & Au, J. L. Drug delivery and transport to solid tumors. *Pharm Res* 20, 1337-1350 (2003).
2 Minchinton, A. I. & Tannock, I. F. Drug penetration in solid tumours. *Nat Rev Cancer* 6, 583-592 (2006).
3 Elliott, N. T. & Yuan, F. A review of three-dimensional in vitro tissue models for drug discovery and transport studies. *J Pharm Sci* 100, 59-74 (2011).
4 Szakacs, G., Varadi, A., Ozvegy-Laczka, C. & Sarkadi, B. The role of ABC transporters in drug absorption, distribution, metabolism, excretion and toxicity (ADME-Tox). *Drug Discov Today* 13, 379-393 (2008).
5 Shugarts, S. & Benet, L. Z. The role of transporters in the pharmacokinetics of orally administered drugs. *Pharm Res* 26, 2039-2054 (2009).
6 Varma, M. V., Ashokraj, Y., Dey, C. S. & Panchagnula, R. P-glycoprotein inhibitors and their screening: a perspective from bioavailability enhancement. *Pharmacol Res* 48, 347-359 (2003).
7 Giacomini, K. M. et al. Membrane transporters in drug development. *Nat Rev Drug Discov* 9, 215-236 (2010).
8 Staud, F., Ceckova, M., Micuda, S. & Pavek, P. Expression and function of p-glycoprotein in normal tissues: effect on pharmacokinetics. *Methods Mol Biol* 596, 199-222 (2010).
9 Szakacs, G., Paterson, J. K., Ludwig, J. A., Booth-Genthe, C. & Gottesman, M. M. Targeting multidrug resistance in cancer. *Nat Rev Drug Discov* 5, 219-234 (2006).
10 Cecchelli, R. et al. Modelling of the blood-brain barrier in drug discovery and development. *Nat Rev Drug Discov* 6, 650-661 (2007).
11 Fellner, S. et al. Transport of paclitaxel (Taxol) across the blood-brain barrier in vitro and in vivo. *J Clin Invest* 110, 1309-1318 (2002).
12 Fromm, M. F. Importance of P-glycoprotein at blood-tissue barriers. *Trends Pharmacol Sci* 25, 423-429 (2004).

13 Letrent, S. P. et al. P-glycoprotein-mediated transport of morphine in brain capillary endothelial cells. *Biochem Pharmacol* 58, 951-957 (1999).
14 Padowski, J. M. & Pollack, G. M. Pharmacokinetic and pharmacodynamic implications of P-glycoprotein modulation. *Methods Mol Biol* 596, 359-384 (2010).
15 Coley, H. M. Overcoming multidrug resistance in cancer: clinical studies of p-glycoprotein inhibitors. *Methods Mol Biol* 596, 341-358 (2010).
16 Ambudkar, S. V. et al. Biochemical, cellular, and pharmacological aspects of the multidrug transporter. *Annu Rev Pharmacol Toxicol* 39, 361-398 (1999).
17 Sikic, B. I. et al. Modulation and prevention of multidrug resistance by inhibitors of P-glycoprotein. *Cancer Chemother Pharmacol* 40 Suppl, S13-19 (1997).
18 Aszalos, A. Drug-drug interactions affected by the transporter protein, P-glycoprotein (ABCB1, MDR1) II. Clinical aspects. *Drug Discov Today* 12, 838-843 (2007).
19 Polli, J. W. et al. Rational use of in vitro P-glycoprotein assays in drug discovery. *J Pharmacol Exp Ther* 299, 620-628 (2001).
20 Rautio, J. et al. In vitro p-glycoprotein inhibition assays for assessment of clinical drug interaction potential of new drug candidates: a recommendation for probe substrates. *Drug Metab Dispos* 34, 786-792 (2006).
21 Keogh, J. P. & Kunta, J. R. Development, validation and utility of an in vitro technique for assessment of potential clinical drug-drug interactions involving P-glycoprotein. *Eur J Pharm Sci* 27, 543-554 (2006).
22 Szeremy, P. et al. Comparison of 3 assay systems using a common probe substrate, calcein AM, for studying P-gp using a selected set of compounds. *J Biomol Screen* 16, 112-119 (2011).
23 Nederman, T Effects of vinblastine and 5-fluorouracil on human glioma and thyroid cancer cell monolayers and spheroids. *Cancer Res* 44, 254-258 (1984).
24 Nederman, T. & Carlsson, J. Penetration and binding of vinblastine and 5-fluorouracil in cellular spheroids. *Cancer Chemother Pharmacol* 13, 131-135 (1984).
25 Risberg, B., Grontoft, O. & Westholm, B. Origin of carcinoma in secretory endometrium—a study using a whole-organ sectioning technique. *Gynecol Oncol* 15, 32-41 (1983).
26 Hwang, C. W., Wu, D. & Edelman, E. R. Physiological transport forces govern drug distribution for stent-based delivery. *Circulation* 104, 600-605 (2001).
27 Youssef, J., Nurse, A. K., Freund, L. B. & Morgan, J. R. Quantification of the forces driving self-assembly of three-dimensional microtissues. *Proc Natl Acad Sci USA* 108, 6993-6998 (2011).
28 Napolitano, A. P. et al. Scaffold-free three-dimensional cell culture utilizing micromolded nonadhesive hydrogels. *Biotechniques* 43, 494, 496-500, doi:000112591[pii] (2007).
29 Nishi, Y. et al. Establishment and characterization of a steroidogenic human granulosa-like tumor cell line, KGN, that expresses functional follicle-stimulating hormone receptor. *Endocrinology* 142, 437-445 (2001).
30 Sadeque, A. J., Wandel, C., He, H., Shah, S. & Wood, A. J. Increased drug delivery to the brain by P-glycoprotein inhibition. *Clin Pharmacol Ther* 68, 231-237 (2000).
31 Fojo, A. T. et al. Expression of a multidrug-resistance gene in human tumors and tissues. *Proc Natl Acad Sci USA* 84, 265-269 (1987).
32 Braga, J., McNally, J. G. & Carmo-Fonseca, M. A reaction-diffusion model to study RNA motion by quantitative fluorescence recovery after photobleaching *Biophys J* 92, 2694-2703 (2007).
33 Essodaigui, M., Broxterman, H. J. & Garnier-Suillerot, A. Kinetic analysis of calcein and calcein-acetoxymethylester efflux mediated by the multidrug resistance protein and P-glycoprotein. *Biochemistry* (1998).
34 Litman, T., Druley, T. E., Stein, W. D. & Bates, S. E. From MDR to MXR: new understanding of multidrug resistance systems, their properties and clinical significance. *Cell Mol Life Sci* 58, 931-959 (2001).
35 Gregor, T., Bialek, W., de Ruyter van Steveninck, R. R., Tank, D. W. & Wieschaus, E. F. Diffusion and scaling during early embryonic pattern formation. *Proc Natl Acad Sci USA* 102, 18403-18407 (2005).
36 Cheema, U., Brown, R. A., Alp, B. & MacRobert, A. J. Spatially defined oxygen gradients and vascular endothelial growth factor expression in an engineered 3D cell model. *Cell Mol Life Sci* 65, 177-186 (2008).
37 Clark, A. R., Stokes, Y. M., Lane, M. & Thompson, J. G. Mathematical modelling of oxygen concentration in bovine and murine cumulus-oocyte complexes. *Reproduction* 131, 999-1006 (2006).
38 Kirkpatrick, J. P., Brizel, D. M. & Dewhirst, M. W. A mathematical model of tumor oxygen and glucose mass transport and metabolism with complex reaction kinetics. *Radiat Res* 159, 336-344 (2003).
39 Chan, H. S. et al. Combining cyclosporin with chemotherapy controls intraocular retinoblastoma without requiring radiation. *Clin Cancer Res* 2, 1499-1508 (1996).
40 Fracasso, P. M. et al. Phase II study of paclitaxel and valspodar (PSC 833) in refractory ovarian carcinoma: a gynecologic oncology group study. *J Clin Oncol* 19, 2975-2982 (2001).
41 Lee, K. S. & Tsien, R. W. Mechanism of calcium channel blockade by verapamil, D600, diltiazem and nitrendipine in single dialysed heart cells. *Nature* 302, 790-794 (1983).
42 Ferry, D. R., Traunecker, H. & Kerr, D. J. Clinical trials of P-glycoprotein reversal in solid tumours. *Eur J Cancer* 32A, 1070-1081 (1996).
43 Susa, M. et al. Multidrug resistance reversal agent, NSC77037, identified with a cell-based screening assay. *J Biomol Screen* 15, 287-296 (2010).
44 Tolcher, A. W. et al. Phase I crossover study of paclitaxel with r-verapamil in patients with metastatic breast cancer. *J Clin Oncol* 14, 1173-1184 (1996).
45 Pampaloni, F., Reynaud, E. G. & Stelzer, E. H. The third dimension bridges the gap between cell culture and live tissue(2007).
46 Dean, D. M. & Morgan, J. R. Cytoskeletal-mediated tension modulates the directed self-assembly of microtissues. *Tissue Eng Part A* 14, 1989-1997, doi:10.1089/ten.tea.2007.0320 (2008).
47 Bao, B., Jiang, J., Yanase, T., Nishi, Y. & Morgan, J. R. Connexon-mediated cell adhesion drives microtissue self-assembly. *FASEB J* 25, 255-264 (2011).
48 Achilli, T. M., McCalla, S., Tripathi, A. & Morgan, J. R. Quantification of the kinetics and extent of self-sorting in three dimensional spheroids. *Tissue Eng Part C Methods* 18, 302-309 (2012).
49 Sharom, F. J. ABC multidrug transporters: structure, function and role in chemoresistance. *Pharmacogenomics* 9 (1), 105-127 (2008)
50 Borges-Walmsley, M. I., McKeegan, K. S., Walmsley, A. R. Structure and function of efflux pumps that confer resistance to drugs. *Biochem. J.* 376, 313-338 (2003)

51 Borst, P. and Elferink, R. O. Mammalian ABC Transporters in Health and Disease. *Annu. Rev. Biochem.* 71, 537-592 (2002)

The relevant teachings of all patents, published applications and references cited herein are incorporated by reference in their entirety.

What is claimed is:

1. A method for treating a tumor, comprising the steps of:
   a) screening for a selected drug that has an effect of inhibiting an efflux pump and not blocking gap junction communication in tumors, the screening method including the steps of,
      i) seeding a cell culture medium that includes a drug to be screened with cells that express an efflux pump and form gap junctions in a non-adherent well to form a cell suspension,
      ii) culturing the cells to thereby form self-assembled spheroids that have multiple layers, including a core and an outer shell,
      iii) incubating the spheroids in the presence of a substrate of the efflux pump to thereby cause at least a portion of the substrate to penetrate the cell, and
      iv) imaging the uptake of the substrate of the efflux pump and the distribution of the substrate within the spheroids, whereby an increase in concentration of substrate in the outer shells of the spheroids relative to that of spheroids that self-assembled in the absence of the drug indicates that the drug inhibits the efflux pump, and an increase of the substrate at the cores of the spheroids relative to that of spheroids that self-assembled in the absence of the drug indicates that gap junction communication has not been blocked by the drug, whereby the drug is designated a selected drug if the efflux pump is inhibited and gap junction communication is not blocked; and
   b) administering the selected drug to a tumor with an anti-cancer drug, thereby treating the tumor.

2. The method of claim 1, wherein the efflux pump is P-glycoprotein.

3. The method of claim 1, wherein the substrate is calcein-AM.

4. The method of claim 1, wherein the efflux pump is P-glycoprotein, and the substrate is calcein-AM.

5. The method of claim 1, further including the step of combining the selected drug that is administered to the tumor with an anti-cancer drug.

6. The method of claim 1, wherein a drug that causes both an increase of substrate in the outer shells of the spheroids relative to that of total spheroids that self-assembled in the absence of the drug, and an increase in substrate at the cores of the spheroid relative to spheroids that self-assembled in the absence of the drug is the selected drug.

7. The method of claim 1, wherein the cells include at least one member selected from the group consisting of granulosa cells, cancer cells, primary human cells, cardiomyocytes, hepatocytes, kidney cells, renal cells, neural cells, skin cells and intestinal epithelial cells.

8. The method of claim 1, further including the step of pre-staining the spheroids by combining the cell culture medium with a stain, and subsequently culturing the cells in the cell culture medium, whereby the resulting spheroids are stained.

9. The method of claim 1, wherein the spheroids have a spheroid height less than about 300 μm.

10. The method of claim 9, wherein the spheroids have a spheroid height less than about 210 μm.

11. The method of claim 10, wherein the spheroids have a spheroid height less than about 205 μm.

12. The method of claim 1, wherein a drug that causes a decrease in the ratio of substrate percent or fraction in the core relative to that of the shell of the spheroids is designated as the selected drug.

13. The method of claim 1, further including the step combining the cell culture medium with an anticancer drug that, if the selected drug were to be administered to a tumor, the selected drug would be administered to the tumor with the anti-cancer drug.

14. The method of claim 1, wherein the tumor includes cells selected from the group consisting of lung, ovarian, colon, liver, renal, neural, pancreatic, prostate, and breast cancer cells.

15. The method of claim 1, wherein the cell culture medium is seeded with KGN cells.

* * * * *